United States Patent [19]

Stienstra

[11] 4,368,438
[45] Jan. 11, 1983

[54] SYSTEM FOR DETECTING SHEET-LIKE OBJECTS

[75] Inventor: Jan B. Stienstra, Venlo, Netherlands

[73] Assignee: OCE-Nederland B.V., Venlo, Netherlands

[21] Appl. No.: 228,332

[22] Filed: Jan. 26, 1981

[51] Int. Cl.³ .......................... H03L 7/08; B65H 7/12
[52] U.S. Cl. .................................... 331/14; 310/336; 331/25; 331/65; 331/155; 340/675
[58] Field of Search ...................... 331/65, 14, 25, 154, 331/155; 310/336; 367/13, 903; 340/673–675; 73/159, 160, 618, 597; 328/5; 271/258, 259

[56] References Cited

U.S. PATENT DOCUMENTS

| 3,392,349 | 2/1967 | Bartley | 331/65 |
| 3,646,372 | 2/1972 | Snellman et al. | 340/675 |
| 3,967,143 | 6/1976 | Watanabe et al. | 310/8.1 |
| 4,066,969 | 1/1978 | Pearce et al. | 340/674 |

FOREIGN PATENT DOCUMENTS 2063540  7/1971  Fed. Rep. of Germany .
1331457  9/1973  United Kingdom .
1533630  11/1978 United Kingdom .

Primary Examiner—Siegfried H. Grimm
Assistant Examiner—Tim A. Wiens
Attorney, Agent, or Firm—Albert C. Johnston

[57] ABSTRACT

In an ultrasonic system for detecting and distinguishing between superimposed and single sheets moving along a transport path, the frequency of the ultrasonic source is kept tuned to the natural frequency of the total system so that the phase displacement detected when a sheet-like object is present between the source and the ultrasonic receiver represents characteristics of the object itself. When no sheet-like object is present the receiver and the source are connected in a feedback circuit producing a certain natural frequency comparable to that which occurs with proximities between a microphone and a loud speaker, and the frequency of an oscillator is tuned to this natural frequency. When a sheet-like object is present the tuned oscillator frequency is applied to the ultrasonic source and its phase is compared with the phase of the ultrasonic signal at the receiver.

5 Claims, 1 Drawing Figure

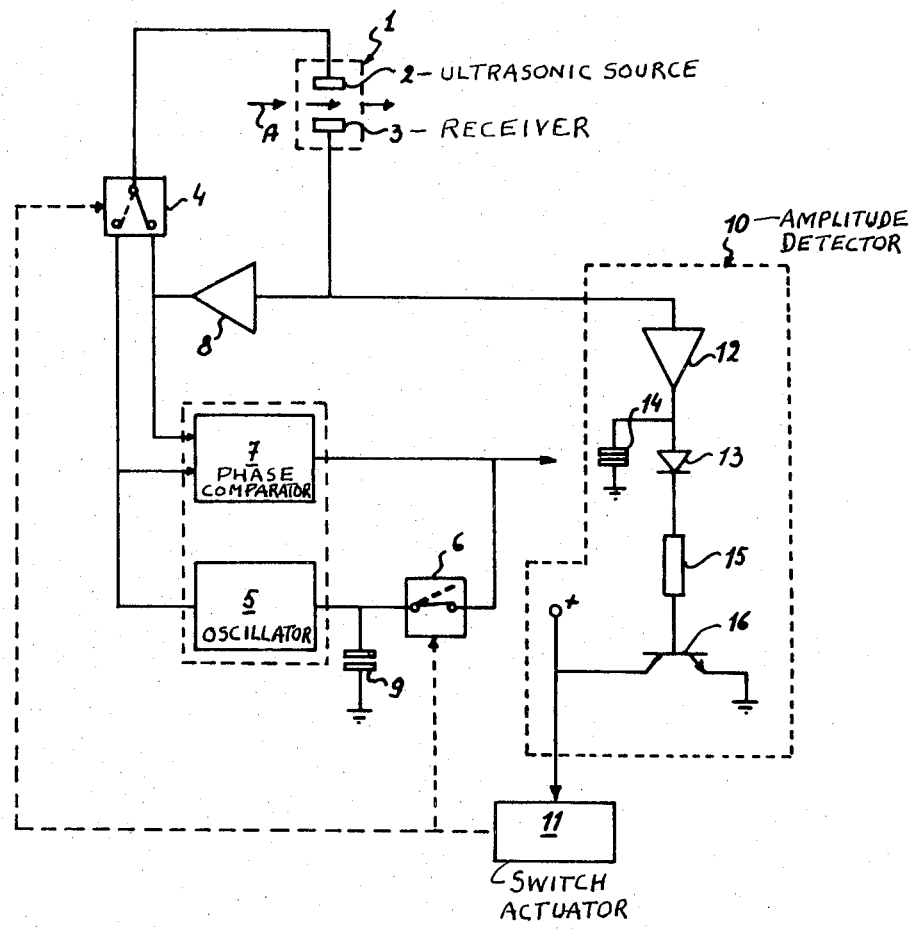

SYSTEM FOR DETECTING SHEET-LIKE OBJECTS

This invention relates to a system for detecting the presence of and distinguishing between superimposed and single sheet-like objects moving along a transport path.

A British Pat. No. 1 533 630 discloses a device for this purpose which comprises an ultrasonic signal source and an ultrasonic signal receiver arranged on opposite sides of a transport path so that a signal from the source passes through the transport path to the receiver, with an oscillator and a phase comparator connected in the system so that the outputs of the oscillator and the receiver form the inputs of the phase comparator. For the operation of this known device the oscillator is set to a certain frequency which is applied to the ultrasonic source. When superimposed sheets instead of a single sheet appear in the gap between the source and the receiver, an increased phase displacement is to be detected between the respective signals of the oscillator and the receiver. This phase shift is related to an initial phase displacement to be detected when no sheet is present in the gap. The initial phase displacement, however, varies in magnitude with variations in the characteristics of the source and the receiver and with variations in temperature and/or humidity, which alter the properties of the air in the gap between the source and receiver. Furthermore, any change in the distance between the source and the receiver will bring about a different phase displacement.

The result of all this is that the known device does not serve its purpose reliably under all circumstances.

The object of the present invention is to provide a system for the stated purpose which avoids the disadvantages of the known device mentioned above.

It has been found that this object can be achieved by a method which comprises passing ultrasonic vibrations through a gap across the transport path from an ultrasonic source to an ultrasonic receiver that produces a signal output representing characteristics of the vibrations received; when no sheet-like object is present in the gap connecting the source with the receiver in a feedback circuit whereby the vibrations in the gap acquire a certain natural frequency determined by then existing characteristics of the elements of the circuit and tuning an oscillator to a frequency corresponding to that natural frequency; and when a sheet-like object is present in the gap applying to the source the tuned frequency of the oscillator and comparing the phase of the vibrations resulting at the receiver with the phase of the oscillator vibrations, thereby producing a signal representing the phase displacement effected by the object.

According to a further feature of the invention, when a sheet-like object ceases to be present in the gap between the source and the receiver a resultant sudden increase in the amplitude of the vibrations at the receiver is detected, and in response to this change of amplitude the ultrasonic source is switched from connection with the oscillator to connection with the receiver in the feedback circuit and the oscillator is tuned to the resultant natural frequency of the vibrations in the gap.

For carrying out the invention, a detecting device or system is provided which comprises an ultrasonic signal source and an ultrasonic signal receiver arranged at opposite sides of the transport path so that the source will transmit ultrasonic signals through the transport path to the receiver, which then forms an output representing characteristics of the signals received, an oscillator having an input to control the frequency of its oscillations, and a phase comparator having inputs connected respectively with the output of the oscillator and the receiver output, together with a first switching means for connecting the output of the phase comparator with the control input of the oscillator, a changeover switching means which in a first position thereof connects the source with the output of the oscillator and in a second position thereof connects the source with the receiver output, and a control circuit including means rendered operative in a period when no sheet-like object is present between the source and the receiver to actuate the first switching means and to dispose the changeover switching means in its second position.

By means of this combination, when no sheet-like object is present in the ultrasonic signal gap the source and the receiver are contained in a "free oscillator" feedback circuit comparable to that occurring with proximities between a microphone and a loud speaker. As a result, a certain natural frequency is set up at a value dependent solely on the elements in the feedback chain, and at the same time the oscillator is tuned to this natural frequency so that when the oscillator is switched over to connection with the source and a sheet-like object is present the phase displacement between the respective vibrations at the source and the receiver is only that which the object itself produces. Furthermore, with this combination the distance between the source and the receiver is no longer critical; so considerable variation of that distance can be tolerated without rendering the detecting system unreliable.

The control circuit of a device according to the invention comprises an amplitude detector connected with the receiver, which detector by reacting to changes in the amplitude of the vibrations at the receiver ensures that the changeover switch will be in its second position only when no sheet-like object is present in the ultrasonic signal gap.

The above-mentioned and other characteristics and advantages of the invention will be apparent from the following description and the accompanying drawing of a preferred embodiment of the invention.

The drawing is a schematic diagram of an electrical circuit for carrying out the invention.

The diagram illustrates a device, or system, according to the invention for detecting doubled or otherwise superimposed sheets and distinguishing them from single sheets moving along a transport path. Such a device can be employed to advantage, for example, in a copying machine. Sheets are moved successively along a transport path schematically indicated by the arrows A. A sheet detector 1 is located beside this transport path and comprises a signal source 2 for the generation of ultrasonic vibrations and a receiver 3 for these vibrations, the source 2 and the receiver 3 being arranged opposite each other on opposite sides of the transport path.

The input of the ultrasonic source 2, in one condition of the system, is connected via a changeover switch 4 with the output of an oscillator 5 which, for example, is a voltage-controlled oscillator (V.C.O.). The oscillator 5 is provided with a control input that can be connected via a switching element 6 with the output of a phase comparator 7. The control input of the oscillator 5 is connected to ground via a capacitor 9 for retaining a control voltage. In a preferred embodiment, for instance, an integrated circuit of the type 4046 is employed for the oscillator 5 and the phase comparator 7.

The phase comparator has a first input connected with the output of oscillator 5, and a second input which is connected via an amplifier 8 with the output of the receiver 3. By means of the changeover element 4 the source 2 can be connected as required either with the oscillator 5 or with the receiver 3.

When the source 2 is connected with the oscillator 5 the source transmits signals at the frequency of the oscillator. In this condition, a direct voltage signal proportional to the phase displacement between the input signals of the comparator 7 is generated in the output of the phase comparator. This phase difference, so the resultant direct voltage signal, has a value when a single sheet is present in the ultrasonic signal gap that differs from its value when superimposed sheets are present there. Consequently, the direct voltage signal of the comparator 7 can be compared with a reference voltage to determine whether a single sheet or a double sheet is present between the source and the receiver.

In the second position of the changeover switch 4, when the source 2 is connected with the receiver 3, a feedback circuit forms which starts to oscillate at a preferred natural frequency. This frequency depends on a number of environmental factors such as the temperature of the air, characteristics of the electrical components in the feedback chain, the distance between the source and the receiver, etc. Upon the occurrence of this natural frequency the oscillator 5 is regulated to exactly the same frequency via the phase comparator 7 and switch 6, this switch having been closed when the changeover element 4 was switched to its second position by the control circuit as described more particularly below.

It results that when changeover switching takes place from the second to the first position, there is always a definite phase difference, which can be substantially 0°, between the signal offered to the source 2 and the signal from the receiver 3, regardless of the tolerances in components and the distance between the source and the receiver. Consequently, the device can operate reliably under all circumstances to produce a signal corresponding to the phase displacement caused by a sheet-like object in the ultrasonic gap, and adjustments are superfluous.

The receiver 3 is also connected with an amplitude detection circuit 10 which reacts to a sudden increase in the amplitude of the signal received by the receiver 3. The amplitude detection circuit 10 comprises an operational amplifier 12, the output of which is connected with the base of a transistor 16 via a rectifier circuit consisting of a diode 13, a capacitor 14 and a resistor 15. The emitter of transistor 16 is connected to ground and the collector is connected with a positive terminal of a voltage supply source via a resistor (not shown).

As soon as the amplitude of the signal of receiver 3 exceeds a certain value the transistor 16 will conduct, so that the potential in the collector will drop. On each occasion when a change occurs in the detecting system from a condition in which a sheet-like object is present to a condition in which no sheet-like object is present, a potential drop occurs in the collector of the transistor 16. The collector of transistor 16 forms the output of the amplitude detection circuit 10, and it is connected with the input of a monostable multivibrator 11. The multivibrator 11 in turn has its output connected with both the changeover switching element 4 and switching element 6 so that, in response to the reaction of circuit 10 to the condition occurring when no sheet-like object is detected between source 2 and receiver 3, the mono-stable multivibrator 11 generates a signal by means of which the changeover switching element 4 connects the source 2 with receiver 3 and the switching element 6 is closed. After only a short period of generation of this signal from the multivibrator 11, the oscillator 5 operates at the frequency to which it is tuned by its control input via switch 6. The capacitor 9 holds the applied control voltage in the control input. The multivibrator signal ceases before a sheet-like object again is present in the ultrasonic gap; so the changeover switch 4 returns to its first position and switch 6 opens, thus reactivating the detecting system at a source frequency tuned to the natural frequency of the system.

It will be apparent to skilled persons that the invention is not restricted to the particular embodiment herein described and illustrated by the drawing and that it can be carried out in other ways and with various modifications of the present disclosure, particularly as regards the electrical components employed, without departing from the substance of the invention which is intended to be defined by the appended claims.

I claim:

1. A method of detecting and distinguishing between superimposed and single sheet-like objects moving along a transport path, which comprises passing ultrasonic vibrations through a gap across the transport path from an ultrasonic source to an ultrasonic receiver that produces a signal output representing characteristics of the vibrations received; when no sheet-like object is present in said gap connecting said source with said receiver in a feedback circuit whereby the vibrations in said gap acquire a certain natural frequency determined by then existing characteristics of the elements of said circuit and tuning an oscillator to a frequency corresponding to that natural frequency; and when a sheet-like object is present in said gap applying to said source the tuned frequency of said oscillator and comparing the phase of the oscillator vibrations resulting at said receiver with the phase of the oscillator vibrations, thereby producing a signal representing the phase displacement effected by the object.

2. A method according to claim 1, and when a sheet-like object ceases to be present in said gap detecting the resultant increase in the amplitude of the vibrations at said receiver and in response thereto switching said source from connection with said oscillator to connection with said receiver in said feedback circuit and tuning said oscillator to the resultant natural frequency of the vibrations in said gap.

3. A device for detecting the presence of and distinguishing between superimposed and single sheet-like objects moving along a transport path, comprising an ultrasonic signal source and an ultrasonic signal receiver arranged at opposite sides of the transport path so that said source will transmit signals through said path to the receiver, said receiver forming an output representing characteristics of the signals received, an oscillator having an input to control the frequency of its oscillations, a phase comparator having inputs connected, respectively, with the output of said oscillator and said receiver output, a first switching means for connecting the output of the phase comparator with said control input of the oscillator, a changeover switching means which in a first position thereof connects said source with the output of said oscillator and in a second position thereof connects said source with said receiver output, and a control circuit including means rendered operative in a period when no sheet-like object is present between said source and said receiver to actuate said first switching means and to dispose said changeover switching means in said second position.

4. A detecting device according to claim 3, said control circuit means comprising an amplitude detector connected with said receiver and which reacts to changes in the amplitude of said receiver output.

5. A detecting device according to claim 4, said amplitude detector comprising a transistor having its collector connected with a voltage source for producing an output signal when the amplitude of said receiver output exceeds a certain value, said control circuit further including a mono-stable multivibrator rendered operative by said output signal to close said first switching means and to dispose said changeover switching means in said second position.

* * * * *